(12) United States Patent
Deleoñ

(10) Patent No.: US 8,915,734 B2
(45) Date of Patent: Dec. 23, 2014

(54) DENTAL SANDING DEVICE

(76) Inventor: José Lisandro Deleoñ, Midlothian, VA (US)

( * ) Notice: Subject to any disclaimer, the term of this patent is extended or adjusted under 35 U.S.C. 154(b) by 117 days.

(21) Appl. No.: 13/068,999

(22) Filed: May 26, 2011

(65) Prior Publication Data

US 2012/0301847 A1  Nov. 29, 2012

(51) Int. Cl.
*A61C 3/06* (2006.01)
*A61C 15/00* (2006.01)

(52) U.S. Cl.
CPC .. *A61C 3/06* (2013.01); *A61C 15/00* (2013.01)
USPC .......................................... 433/142; 433/141

(58) Field of Classification Search
USPC ............. 433/39–40, 125, 142, 146, 148, 166, 433/149, 141; 132/175.6, 76.5, 323, 328, 132/326–327, 321, 329; 451/523, 527
See application file for complete search history.

(56) References Cited

U.S. PATENT DOCUMENTS

| | | | | |
|---|---|---|---|---|
| 1,570,357 A | * | 1/1926 | Lawrenz | 132/324 |
| 4,690,642 A | * | 9/1987 | Kyotani | 433/142 |
| D323,723 S | * | 2/1992 | Chung | D28/68 |
| 5,829,458 A | * | 11/1998 | Chodorow | 132/323 |
| 6,089,241 A | * | 7/2000 | Lo | 132/326 |
| 7,455,521 B2 | * | 11/2008 | Fishburne, Jr. | 433/142 |
| 2005/0058963 A1 | * | 3/2005 | Stockstill | 433/166 |
| 2006/0127845 A1 | * | 6/2006 | Khouri | 433/142 |
| 2008/0081313 A1 | * | 4/2008 | Kim | 433/142 |
| 2010/0279252 A1 | * | 11/2010 | Navarro | 433/118 |

* cited by examiner

*Primary Examiner* — Edward Moran
(74) *Attorney, Agent, or Firm* — Brian J. Teague

(57) ABSTRACT

The current invention refers to a device for the removal of residues that have not been removed after the repair of teeth. It enables easier sanding between teeth, provides greater support, and requires less time for the oral cavity to be open. It is lubricant, electricity, and battery free. The surfaces of this invention are smooth with rounded edges, and can sand both the fronts and the backs of the teeth. The current invention will enable dentists throughout the world easier manipulation in the process of removing residues after teeth repair and will only require the use of one hand.

8 Claims, 3 Drawing Sheets

DENTAL SANDING DEVICE

FIELD OF THE INVENTION

The current invention refers to a device for the removal of residues that have not been removed after the repair of teeth.

BACKGROUND

Dental sanding devices are well known, and used by dentists in the removal of residues or surplus material after having performed a repair. One drawback of current dental sanding devices is that current devices require dentists to use both hands in order to manipulate the type of sanding device currently available. As such, current dental sanding devices are more complicated to use and therefore result in the patient being kept with his/her oral cavity open for a longer period of time.

BRIEF SUMMARY OF THE INVENTION

In one embodiment of the invention, a dental sanding device comprises a body, a first sanding strip, and a second sanding strip. The body comprises a handle, a first arch, and second arch. The first sanding strip is supported by the first arch and has an abrasive side and an opposing non-abrasive side. The second sanding strip is supported by the second arch and has an abrasive side and an opposing non-abrasive side. The abrasive side of the first sanding strip and the abrasive side of the second sanding strip each face an opposing side of the body.

Grooves may be defined in the first arch and in the second arch. The first sanding strip may be disposed in the grooves of the first arch. The second sanding strip may be disposed in the grooves of the second arch.

The first sanding strip may be heat sealed in the grooves of the first arch, and the second sanding strip may be heat sealed in the grooves of the second arch.

BRIEF DESCRIPTION OF THE SEVERAL VIEWS OF THE DRAWING(S)

Reference is made herein to the accompanying drawings, which are not necessarily drawn to scale, and wherein.

DETAILED DESCRIPTION

Going into greater detail, this invention refers to a design perfected in devices that enable the adaptation of a type of sander and removal of residues of different types used by dentists when teeth are repaired. It is easily used, is light and portable, and is made out of a low cost plastic or elastomer.

The device makes sanding between teeth easier. Said device comprises three pieces, one that comprises the framework, and the other two comprising the sanding material that are situated in an adequate manner. The framework permits the desired function. Said assembled pieces enable the use of only one hand to perform the sanding operation. The sanding pieces are placed in different positions to meet the objective of removing residues left in the repair of teeth. We must keep in mind that there are different types of materials used to repair teeth like resins and materials like silver and others.

We must also keep in mind that there are different types of sanding materials produced by companies and said materials are used by dentists worldwide. With this device, we have the advantage that said sanding materials can be placed in the device, which is a plastic or elastomer framework that is relatively resistant when used, and whose edges are rounded, thus avoiding laceration of the oral cavity. We must recommend it be used responsibly by trained dentists.

The framework is molded by previously established matrices or molds that contain grooves in order to couple the different types of sanding material previously made by other manufacturers that produce said product.

When said sanding material is attached to the plastic framework, containing grooves for its attachment, said design provides an adequate means for sanding.

The sealing of the grooves with the different types of sanding material is done through heat at the grooves, which is made possible by the material from which it is made.

The movement of said device is back and forth permitting its function, between the teeth that were repaired, being careful not to injure the upper and lower gum tissue.

Additionally, we mention that said device does not require any type of lubricant, electricity or batteries as it is manually used for its adequate function. It should also be taken into account that said device has a totally smooth side that permits movement between teeth.

Figure 1:
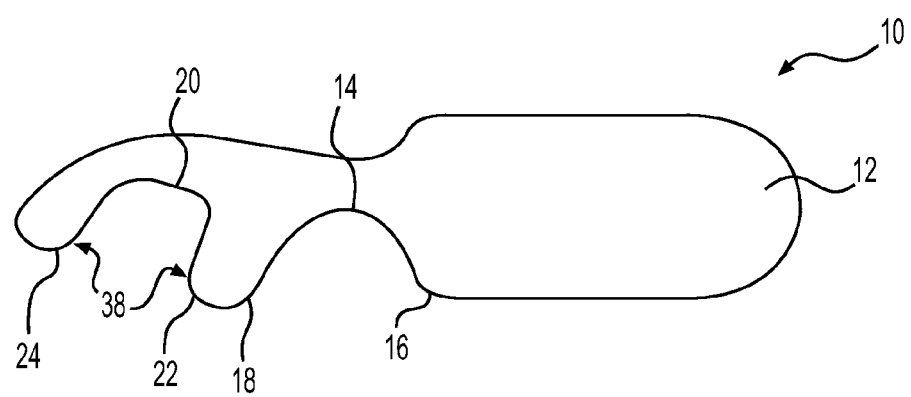
FIG. 1 is side view of a dental sanding device (with the sanding material omitted), in accordance with embodiments of the invention.

Figure number one shows us the plastic frame without the strips of sanding material described below. FIG. 1 shows a dental sanding device 10 comprising a body. The body has a handle 12 and two arches. A first arch 14 is formed between a proximal end 16 and a distal end 18, while a second arch is formed between a proximal end 22 and a distal end 24.

Figure 2:
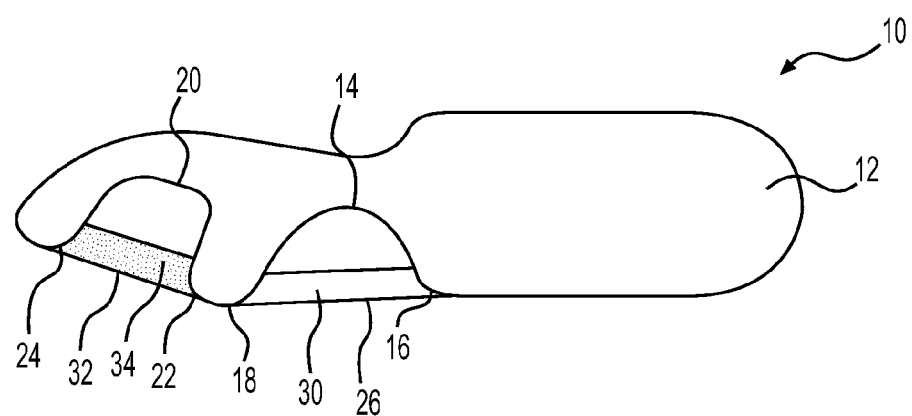
FIG. 2 is a side view of the dental sanding device of FIG. 1, with the sanding material illustrated.
Figure 3:
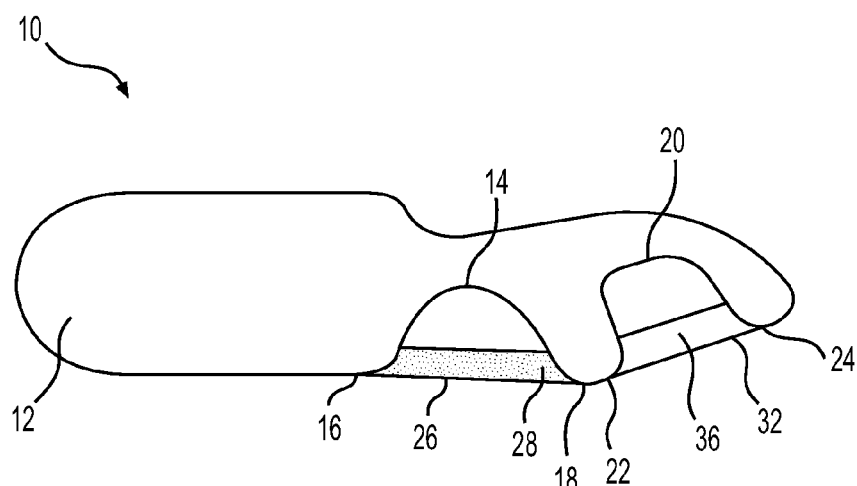
FIG. 3 is slight perspective view of the opposite side of the dental sanding device of FIGS. 1, 2.

For descriptive purposes only, the side visible in FIGS. 1 and 2 will be termed the "front" side and the side visible in FIG. 3 will be termed the "back" side. FIGS. 2 and 3 illustrate a first strip of sanding material 26 supported by the first arch and a second strip of sanding material 32 supported by the second arch. Each strip of sanding material has an abrasive side with an abrasive portion and a smooth (non-abrasive) side with a non-abrasive portion (30;36). Importantly, the abrasive side of the first strip of sanding material is on an opposing side of the device from the abrasive side of the second strip of sanding material.

In figure two, the first strip of sanding material supported by the first arch has an abrasive side with an abrasive portion toward the front side of the device and a non-abrasive side with a non-abrasive portion toward the back side of the device. In other words, the side of the first sanding strip that sands 28 is toward the front side of the device and the back side of the sanding strip is the smooth (non-abrasive) side with non-abrasive portion. In figure three, the second strip of sanding material supported by the second arch has an abrasive side with an abrasive portion toward the back side of the device and a non-abrasive side with a non-abrasive portion toward the front side of the device. In other words, the side of the second sanding strip that sands 34 is toward the back side of the device and the front side of the sanding strip is the smooth (non-abrasive) side with non-abrasive portion. Thus, the dental sanding device of embodiments of the invention enable a dentist to sand either the front or back side of the teeth according to what is needed to complete the sanding process effectively and without problems, resulting from the location of the sanders on said device. Only one hand is used due to the device's design providing greater support than the traditional sanders which require use of two hands.

A dental sanding device of embodiments of the invention may have an exemplary size of 9.5 cm length; 2.2 cm height, and 0.2 cm thickness, thereby permitting work to be done inside the oral cavity.

The device is made of plastic or elastomer showing the previously made frame or base by a matrix with rounded edges in order to prevent any type of laceration with said frame or base in the oral cavity with responsible use.

The device, due to its form and design, permits the use of only one hand, giving better support, in contrast to traditional sanders which require both hands. Grooves 38 are located at the proximal and distal ends of the arches, and show where the different types of sanding materials are attached, according to the need to remove the different materials used by dentists.

In figure two, the separation between the arches of the frame are shown, and the positions of the different types of sanders. As an example in this figure, the second sanding strip 34 has an exemplary 1.8 cm distance and the first sanding strip is 2.2 cm. The measurements can vary according to the manufacturer's criteria. It must be kept in mind that the type of sanding material used by dentists varies according to the type of material that would like to be removed. The sanding material varies according to the manufacturer.

Figure three gives an approximate thickness of the frame. It shows how the sanding strips are in different positions, giving it greater maneuverability and exerting greater pressure where it is desired.

As illustrated in the sample drawings with their designated references in general, a dental sanding device of embodiments of the invention incorporates a preferred form of the invention, comprises grooves 38 in the arches and wherein the sanding strips are attached in different positions. Additionally, the sanding strips are sealed in the grooves by heat or adhesive so that the arches maintain the sander firmly and achieve the desired outcome for dental use.

The invention claimed is:

1. A dental sanding device comprising:
a body comprising (i) a handle, (ii) a first arch having an end proximal to the handle, an end distal to the handle, and an opening therebetween, (iii) a second arch having an end proximal to the handle, an end distal to the handle, and an opening therebetween, the distal end of the first arch abutting the proximal end of the second arch, the distal end of the second arch being distal to the proximal end of the second arch;
a first sanding strip supported by the first arch, the first sanding strip having an abrasive side with an abrasive portion and an opposing non-abrasive side with a non-abrasive portion; and
a second sanding strip supported by the second arch, the second sanding strip having an abrasive side with an abrasive portion and an opposing non-abrasive side with a non-abrasive portion;
wherein the abrasive side of the first sanding strip and the abrasive side of the second sanding strip each face an opposing lateral side of the body; and wherein the abrasive portions and the non-abrasive portions of the first and second sanding strips span entirely across the respective arch openings from the proximal end to the distal end of the respective arches.

2. The dental sanding device of claim 1, wherein grooves are defined in the first arch, wherein grooves are defined in the second arch, wherein the first sanding strip is disposed in the grooves of the first arch, and wherein the second sanding strip is disposed in the grooves of the second arch.

3. The dental sanding device of claim 2, wherein the first sanding strip is heat sealed in the grooves of the first arch, and wherein the second sanding strip is heat sealed in the grooves of the second arch.

4. A dental sanding device comprising:
a body comprising a handle, a first arch having an opening, and second arch having an opening, the opening of the first arch and the opening of the second arch being arranged end-to-end;
a first sanding strip supported by the first arch, the first sanding strip having an abrasive side with an abrasive portion and an opposing non-abrasive side with a non-abrasive portion; and
a second sanding strip supported by the second arch, the second sanding strip having an abrasive side with an abrasive portion and an opposing non-abrasive side with non-abrasive portion;
wherein the abrasive side of the first sanding strip and the abrasive side of the second sanding strip each face an opposing lateral side of the body;
wherein the non-abrasive side of the first sanding strip and the non-abrasive side of the second sanding strip each face an opposing lateral side of the body;
wherein the abrasive side of the first sanding strip and the non-abrasive side of the second sanding strip each face a same lateral side of the body; and
wherein the non-abrasive side of the first sanding strip and the abrasive side of the second sanding strip each face a same lateral side of the body and wherein the abrasive portions and the non-abrasive portions of the first and second sanding strips span entirely across the respective arch openings from a proximal end to a distal end of the respective arches.

5. The dental sanding device of claim 4, wherein grooves are defined in the first arch, wherein grooves are defined in the second arch, wherein the first sanding strip is disposed in the grooves of the first arch, and wherein the second sanding strip is disposed in the grooves of the second arch.

6. The dental sanding device of claim 5, wherein the first sanding strip is heat sealed in the grooves of the first arch, and wherein the second sanding strip is heat sealed in the grooves of the second arch.

7. The dental sanding device of claim 1, wherein the second sanding strip is at an obtuse angle to the first sanding strip.

8. The dental sanding device of claim 4, wherein the second sanding strip is at an obtuse angle to the first sanding strip.

* * * * *